(12) United States Patent
Cartwright et al.

(10) Patent No.: US 7,602,933 B2
(45) Date of Patent: Oct. 13, 2009

(54) CONFORMABLE EAR PIECE AND METHOD OF USING AND MAKING SAME

(75) Inventors: Kristopher L. Cartwright, Colorado Springs, CO (US); Richard B. Morgan, Woodland Park, CO (US)

(73) Assignee: Westone Laboratories, Inc., Colorado Springs, CO (US)

( * ) Notice: Subject to any disclaimer, the term of this patent is extended or adjusted under 35 U.S.C. 154(b) by 969 days.

(21) Appl. No.: 10/952,683

(22) Filed: Sep. 28, 2004

(65) Prior Publication Data

US 2006/0067551 A1    Mar. 30, 2006

(51) Int. Cl.
    *H04R 25/00* (2006.01)
(52) U.S. Cl. .................. 381/380; 381/328; 128/867
(58) Field of Classification Search .............. 381/72, 381/327–328, 330, 380–381; 181/128–135; 128/857, 864–865, 867
See application file for complete search history.

(56) References Cited

U.S. PATENT DOCUMENTS

| 3,050,056 | A | * | 8/1962 | Dressler | 128/864 |
| 4,338,929 | A | * | 7/1982 | Lundin et al. | 128/864 |
| 4,880,076 | A | | 11/1989 | Ahlberg et al. | 181/130 |
| 5,247,946 | A | | 9/1993 | Holder | 128/864 |
| 6,000,492 | A | * | 12/1999 | Puthuff et al. | 181/135 |
| 6,513,621 | B1 | * | 2/2003 | Deslauriers et al. | 181/130 |

* cited by examiner

*Primary Examiner*—Suhan Ni
(74) *Attorney, Agent, or Firm*—Sheridan Ross P.C.

(57) ABSTRACT

An ear piece device comprising a generally cone-shaped article made of pliable material dimensioned for fitting the ear canal of a user. In one embodiment, one canal extends through a portion of the ear piece to provide an opening for communication between a person's inner ear and an environment outside the person's ear. The ear piece has a plurality of fold lines provided to facilitate the reversible collapsing of the cone into a star-like configuration when sufficient outside pressure is applied thereto.

8 Claims, 2 Drawing Sheets

CONFORMABLE EAR PIECE AND METHOD OF USING AND MAKING SAME

FIELD OF THE INVENTION

The present invention is directed to a device for insertion into an orifice of a living animal, and more particularly, is directed to an ear piece designed so as to reversibly compress and conform to a person's ear canal.

BACKGROUND OF THE INVENTION

A variety of ear pieces exist for various uses, including use with respect to hearing aids, stethoscopes, sound blocking devices, sound generation devices and swim ear plugs. Given the sensitive tissues that line a person's ear and the prospect that a person may repeatedly use such ear pieces over extended periods of time, it is important to have the ear piece "fit" within the ear in a comfortable fashion. Moreover, it is often desirable for an ear piece to substantially contact surrounding ear canal tissue so as to maximize the effectiveness of the ear piece, whether it be to block out certain sounds from passing through the inner ear canal to a person's ear drum, or alternatively to ensure that only desirable sounds are transmitted to the ear drum, rather than undesired ambient noises.

The present invention is directed to a device that provides an easy and effective fit, without undesirable noisy feedback and that improves user comfort when inserted in the aural orifice.

SUMMARY OF THE INVENTION

One aspect of the present invention as directed to an ear piece that is capable of forming a substantially air tight and water tight seal when inserted into an ear canal. In one embodiment, the ear piece is designed so as to be capable of attenuating sound to protect the user from undesired ambient noises. In a preferred embodiment, the ear piece is made of silicone and can form a substantially tight seal in a person's ear canal. Other embodiments, however, may comprise closed-cell foam, or a combination of materials, including silicone, rubber, plastics and other various types of foams. In certain embodiments, the ear piece provides for rapid equalization of air pressure to reduce possible discomfort caused by air pressure differences between the ear canal and the ambient pressure.

In one embodiment, the ear piece has a generally cone-shaped appearance (or otherwise referred to as a "bullet-shape") and at the conical end, a central longitudinal passage is provided which can further be associated with various tube-like structures. In one embodiment the tube-like structure is adapted to connect to appropriate tubing so as to join the ear piece to another item, whereby sound may be communicated through the tubing. The ear piece itself can be compressed (e.g., by a person's fingers) so as to be freely insertable into an external ear canal of a user and to become wedged in the canal when the ear piece is allowed to recover from its compressed configuration.

The material comprising the ear piece is preferably a highly flexible and/or pliable material that can be compressed in a fashion so that distinct folds are formed in the material, creating what appears to be a "star-like" configuration when fully compressed along each fold line. Any number of "star points" in such a star configuration can be provided by adjusting the number of fold lines in the conical structure itself. The fold lines need not traverse the entire ear piece cone structure, but rather, may extend only partially from one end or the other of the cone-like structure or, just in the middle of the structure or alternatively can extend the entire length thereof. The fold lines themselves can be depressions in the flexible material itself, physically scored into the material, or otherwise provided. In a preferred embodiment, the ear piece is molded from a flexible material, such as silicone, and the fold lines are created through a molding process. In a preferred embodiment, the compression of the ear piece generates a configuration that is not a flat two-dimensional cone, but rather, contains at least one other folded dimension. For example, a star-like pattern (as viewed from one or the other end of the cone-shaped ear piece) may have at least three star points, more preferably at least four, even more preferably at least five, and can have as many star points as desired. Preferably, the fold lines are spaced a predetermined distance apart, preferably at least about 3 mm, more preferably, at least about 5 mm and in other embodiments, at least about 7 mm.

The size of the cone-shaped ear piece may vary, but is preferably of a relatively standard size to fit within a person's ear canal. Given the variation in individual's ear canal diameters, however, it is also within the scope of the present invention to have various sized ear pieces to properly fit the variety of ear canals that may exist in any given population. For example, a smaller sized ear piece can be provided to fit an infant or small children's ear canal. In another embodiment, the wide end of the bullet shape of the cone can be adjusted to fit a particular person's ear canal. For example, the widest end of the cone can be cut (e.g., along predetermined latitudinal lines) to leave a smaller diameter cone. From a manufacturing standpoint, the unique "star-like" compression characteristics of the ear piece facilitates the production of a soft, pliable ear piece that can be readily molded and mass produced in various colors, particular configurations, etc., without particular worries as to the predetermined dimensions of traditional plastic ear pieces.

The present invention provides an ear piece for use, for example, with personal head phones, hearing aids, stethoscopes, ear plugs, etc. that can be worn continuously with comfort. In addition to its improved comfort afforded by its construction, the present invention facilitates the confidence of a user that not only will the ear piece will be retained during use, but will conform to the specific shape of the wearer's ear canal and also be readily removable when desired. In one embodiment, the present invention provides a user with a disposable ear piece for a hearing aid, stethoscope or any other type of application requiring such an ear piece. No special fitting by an audiologist is required due to the self-conforming nature of the present invention to a person's aural canal.

It is within the scope of the present invention to have ear pieces of different geometrical configurations. For example, although a conical configuration is set forth in the drawings, other geometrically configured ear pieces, such as, for example, that illustrated in U.S. Pat. No. 6,513,621 to Deslauriers et al., can be manufactured with appropriate fold or score lines so as to facilitate the collapsibility of such ear pieces in accordance with the present invention.

In preferred embodiments for sound transmission uses, a central auditory passage is provided to facilitate the transmission of sound through the ear piece. In other embodiments, such as ear plugs for swimming and sound blocking devices, etc., no aperture is formed in the ear piece. In one embodiment, an ear piece can be "customized" by having the ability to cut-out or push-out predetermined portions of material to create a central orifice. Separate tube-like or threaded adaptor pieces can then be associated with the ear piece, held in place by friction, screwing or by adhesive means. While preferably the entire ear piece device is made of pliant material, it is also within the scope of the present invention to have certain rigid and/or less flexible elements associated with the more pliant components of the ear piece. For example, a more rigid central auditory canal (see 16 on FIG. 4) can be associated with the more pliant surrounding compressible/foldable material.

Preferably, the disclosed ear piece is manufactured from a soft elastomeric material, such as PVC, other thermal plastic or liquid injection molded material, such as silicone, but it is also possible to manufacture it from other suitable elastomeric materials. The ear piece itself can be impregnated with anti-microbial agents to reduce the number of times the ear piece (if not disposable) must be sterilized in order to maintain a relatively bacteria-free ear piece. In certain embodiments, the ear piece itself can be disposable to facilitate sanitary and hygienic purposes. The particular wall thickness of the ear piece can be adjusted to facilitate desired folding characteristics and rigidity within the ear canal, to ensure a good acoustic seal and so that appropriate "pull out" tensions can be achieved.

Various ways can be employed to connect the collapsible ear piece of the present invention to sound transmitting devices. For example, a threaded embodiment can be employed to fit certain stethoscope ear tips. Other embodiments, however, rely upon bayonet mounts, simple telescoping tube attachments, etc. to connect or attach to other devices.

In certain embodiments of the present invention, the primary benefit of the collapsible star-design of the flexible article is to allow at least one end or tip of the article to be inserted into a user's ear in a shape distorted from its relaxed (extended) shape. It can then expand and/or return to a configuration that does not create distortion or "pleats" in the exterior surface of the article. Side views of the expanded article configurations can be of various geometric shapes, including, but not limited to oval and round. The present invention therefore facilitates the production and use of an ear tip device that is able to fit a wide variety of ear canal shapes and to provide an enhanced acoustic seal. The inside diameter of the article of the present invention can be modified to accept a variety of stem sizes, thus facilitating connection of the ear tip piece with various and distinct articles, including, but not limited to head phones, stethoscopes, hearing aids, sound blocking devices, etc. The outside diameter of the ear tips of the present invention can also be made in various sizes so as to fit a wide variety of ear shapes and sizes.

One embodiment of the present invention is directed to an ear piece device comprising a generally cone-shaped article comprising pliable material dimensioned for fitting the outer ear canal of a user. The ear piece has a first end and a second end and at least one canal extending substantially from the first end toward the second end. The canal provides an opening that communicates between a person's inner ear and an environment outside the person's ear. The ear piece preferably has a plurality of fold lines provided in or otherwise associated with its material in order to facilitate the collapsing (e.g., along predetermined fold lines) of the generally cone-shaped article when sufficient outside pressure is applied thereto. The ear piece is compressible into star-like configurations having at least three star points, more preferably, at least four points, and even more preferably, five or more star points. The ear piece device of the present invention can be used in conjunction with various articles including a stethoscope, an MP3 player, a sound recording device, a hearing aid, an aquatic blocking device (e.g., ear plugs), sound blocking devices (for example, by use in airports, manufacturing environments, etc.). Preferably, the ear piece is made from a pliable and compressible material such as plastic, silicone, rubber, synthetic polymer, foam material and natural polymers.

An ear piece of the present invention is preferably adapted to be inserted in the ear canal of a user and comprises material that has at least three weakened longitudinally extending portions that facilitate the material being collapsible into a first non-flat collapsed position and extendible into a second extended position. The first position presents at least three distinct folded members. When expanded, however, into the second position, the ear piece is substantially devoid of the presentation of such members (e.g., the star-like configuration is expanded so that no "star points" are discernable).

The present invention also encompasses a method of making various configured ear pieces described herein. The steps of manufacturing such ear pieces generally comprise providing a generally cone-shaped article made of pliable material and forming at least three fold lines along an axially dimension of the cone-shaped article so as to facilitate the reversible compression of the article into a star-shaped configuration. Preferably, the forming of the at least three fold lines comprises a molding operation. In other embodiments, however, scoring of the material can be employed to provide weakened points to facilitate folding of the article.

In a preferred embodiment, molded or scored grooves are provided in the material making up the ear piece. Such grooves are deep enough to facilitate desired folding characteristics of the ear piece. In one embodiment, the grooves are at least about ¼ of the entire depth of the material's thickness comprising the ear piece. Other suitable groove depths can be selected, for example, at least ½ of the thickness of the material, at least ¾ of the thickness of the material, etc. In less preferred embodiments, actual slits can be cut into the material so that a desired star-like folding configuration can be achieved. Upon expansion of the ear piece device, however, such slits are effectively closed by the expanding configuration of the ear piece.

This summary of the invention is not intended to fully describe each and every potentially important aspect of the present invention. One of skill in the art will understand from the entire specification, including the drawings, claims, detailed description, etc., the full scope of the present invention.

DETAILED DESCRIPTION

Figure 2:
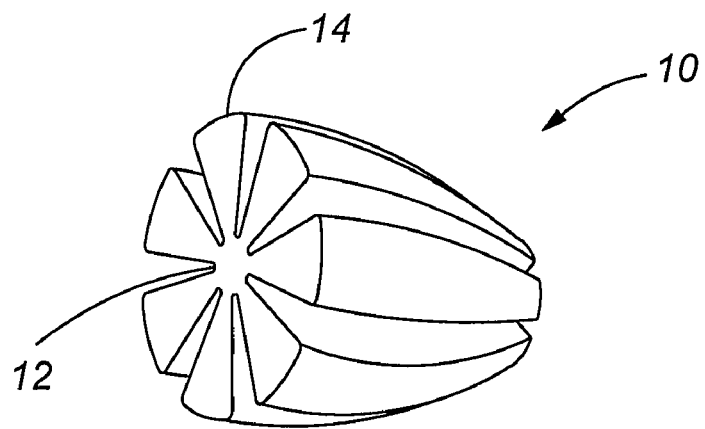
FIG. 2 is a further perspective view of an embodiment of the present invention.
Figure 1:
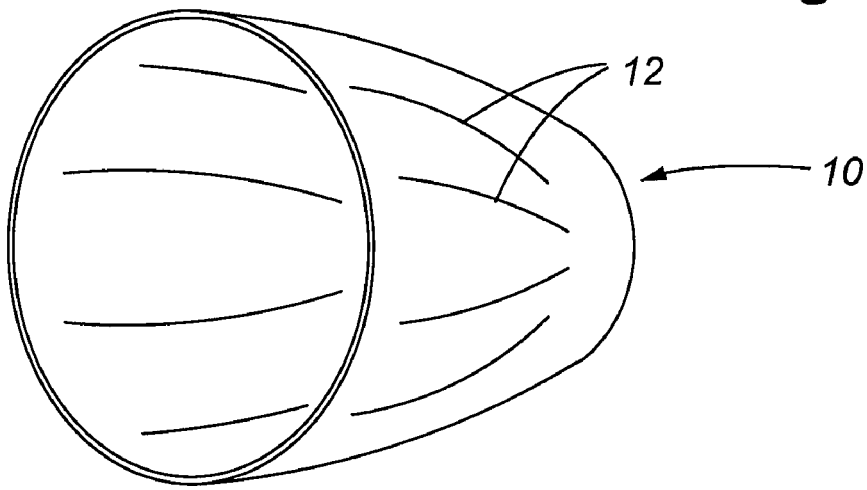
FIG. 1 is a perspective view of one embodiment of the present invention in an expanded, non-completed configuration.
Figure 3:
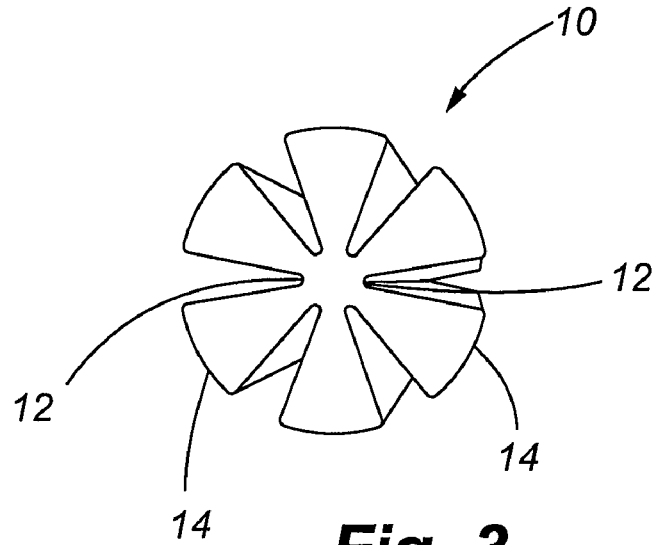
FIG. 3 is a partial perspective view of one end of a compressed configuration of another embodiment of the present invention.

The ear piece 10 of the present invention is provided with fold lines 12 (e.g., at least three) spaced about the periphery of either the internal or external surface of the ear piece 10. The fold lines 12 permit the ear piece 10 to be collapsible and/or contortable, into a "star-like" configuration, whereby various star points 14 are formed, with the fold lines 12 being pushed into the center of the star-like configuration. FIG. 2 illustrates one embodiment of the present invention having 7 star points that correspond to the score lines and/or fold lines 12 of such an embodiment. FIG. 3 shows a 6-point star-like configuration from one end of the device.

Figure 4:
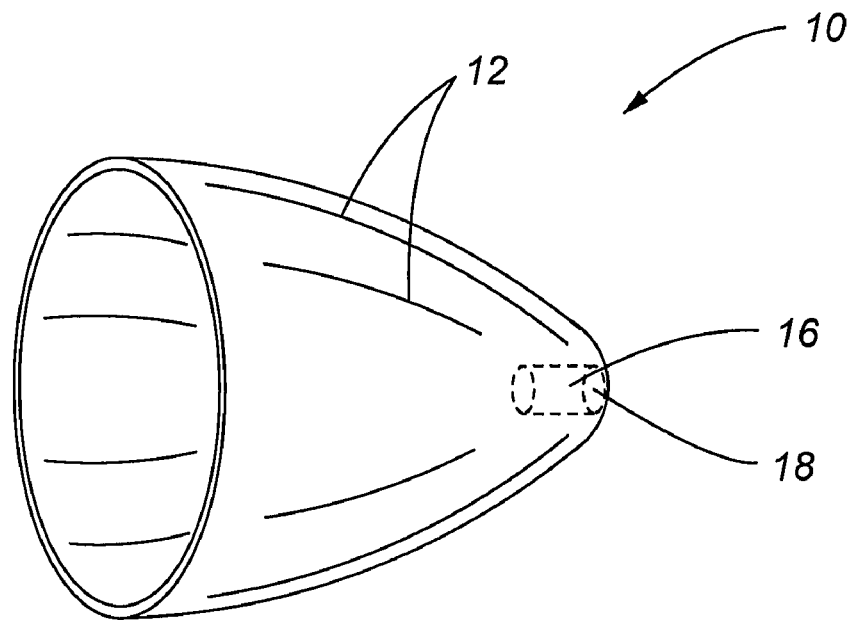
FIG. 4 is a side perspective view of one embodiment of the present invention showing an internal connection tube.

FIG. 4 is a side perspective view of one embodiment of the present invention showing a tube structure 16 that connects with a central orifice 18, such tube structure 16 facilitating connection with tubing that transmits sound there through.

Figure 5:
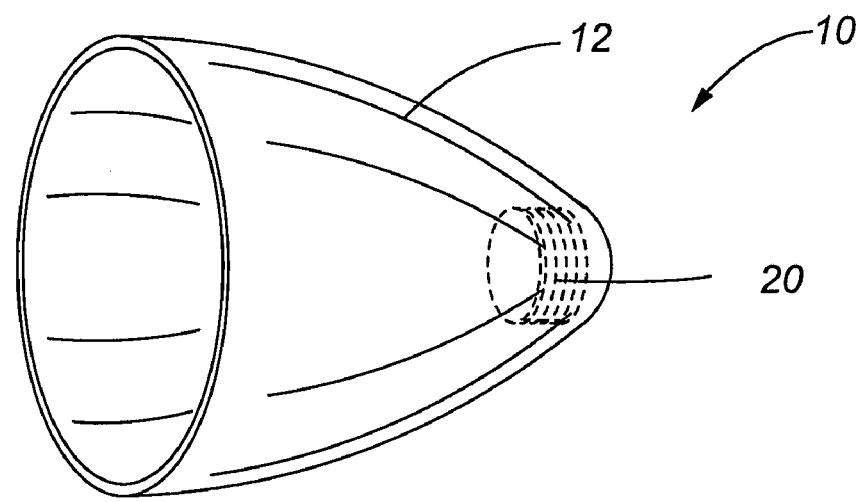
FIG. 5 is a side perspective view of another embodiment of the present invention having a threaded screw connector orifice.

FIG. 5 is yet another embodiment of the present invention where a threaded aperture is provided for connection to various mating threaded devices, such as stethoscopes, hearing aids, etc.

One aspect of the present invention is directed to manufacturing an ear piece designed to reversibly compress and conform to a person's ear canal such that the ear piece can be distorted from its relaxed shape into an oval configuration without creating significant distortion or pleats in the exterior surface of the ear piece. To produce such an article, conventional casting processes can be employed that involve the use of a single or multi-cavity two-part mold which can be made from aluminum or steel. A two-part silicon cone is preferably mixed and poured into such mold and when the silicon is appropriately cured, the mold is opened and the parts removed. The articles of the present invention can also be manufactured through a liquid silicon injection technique. This method may employ the use of steel tools that can be heated and subsequently mounted in an injection machine. The mold closes and a one-part silicone is then injected into the mold. The heated mold cures the silicone and when the mold is opened up, the parts are removed. In alternative embodiments, ear piece articles can be made of PVC, rather than silicone, and standard injection molding processes can be used for such manufacturing operations. Other various manufacturing techniques, which will be apparent to those of skill in the art, can be employed to manufacture the present articles. In certain embodiments, the molds employed have distinct configurations and characteristics to impart a pleat or depression in the surface of the article (e.g., either on the exterior or the interior of the article), thus providing the ability of forming compressible star-configurations to achieve the purposes of the present invention.

While the various illustrated embodiments are particularly directed to use in the ear canal of a person, one of skill in the art will comprehend and understand that the inventive concept can be utilized in other orifices of either people or animals, and in particular, companion animals. For example, other applications of the present invention can be utilized for nasal passages in order to open such nasal passages a slight degree from the interior of such nasal passages. This aspect of the present invention facilitates a final result similar to that achieved using Breathe Right® devices that apply adhesive outward projecting forces to open nasal passages. Suitable modifications in the size, length and shape/geometry configurations of the present invention can be made to facilitate particular uses, for example, in the above-referenced nasal passage usage. Other suitable uses for the present invention when inserted into a nasal passage are directed to nasal drainage systems, ventilation and other respiratory uses, etc.

While various embodiments of the present invention have been described in detail, it will be apparent that further modifications and adaptations of the invention will occur to those skilled in the art. It is to be expressly understood that such modifications and adaptations are within the spirit and scope of the present invention.

What is claimed is:

1. An ear piece device, comprising a generally cone-shaped article comprising pliable material dimensioned for fitting the outer ear canal of a user, said article having a first end and a second end and at least one canal extending substantially from said first end toward said second end, said canal providing an opening that communicates between a person's inner ear and an environment outside the person's ear, said ear piece having a plurality of fold lines provided in said material to facilitate the collapsing of said cone when sufficient outside pressure is applied thereto, said cone being compressible into a star-like configuration having at least three star points.

2. The ear piece as set forth in claim 1, wherein said ear piece is used in conjunction with a stethoscope.

3. The ear piece as set forth in claim 1, wherein said ear piece is used in conjunction with an MP3 player.

4. The ear piece as set forth in claim 1, wherein said ear piece is used in conjunction with a sound recording device.

5. The ear piece as set forth in claim 1, wherein said ear piece is made of a material selected from the group consisting of plastic, rubber, synthetic polymer and natural polymer.

6. An ear piece device, comprising a generally cone-shaped article comprising pliable material dimensioned for fitting the outer ear canal of a user, said article having a first end and a second end, said ear piece having a plurality of fold lines provided in said material to facilitate the collapsing of said cone when sufficient outside pressure is applied thereto, said cone being compressible into a star-like configuration having at least three star points.

7. The ear piece as set forth in claim 6, wherein said ear piece is used in conjunction with a sound blocking ear plug.

8. The ear piece as set forth in claim 6, wherein said ear piece is used in conjunction with a water swimmer's ear plug.

* * * * *